United States Patent [19]

Deno

[11] 4,045,498

[45] Aug. 30, 1977

[54] METHOD OF HYDROXYLATION

[75] Inventor: Norman C. Deno, State College, Pa.

[73] Assignee: Fats and Proteins Research Foundation, Inc., Des Plaines, Ill.

[21] Appl. No.: 622,661

[22] Filed: Oct. 15, 1975

[51] Int. Cl.[2] ...................... C07C 29/00; C07C 31/18

[52] U.S. Cl. ............................... 260/617 R; 260/400; 260/404; 260/408; 260/410; 260/410.9 R; 260/413; 260/456 R; 260/457; 260/484 R; 260/487; 260/535 R; 260/583 D; 260/583 DD; 260/586 R; 260/593 R; 260/598; 260/601 R; 260/611 R; 260/614 R; 260/631 R; 260/632 R; 260/635 R; 260/642 R

[58] Field of Search .......... 260/617 R, 631 R, 632 R, 260/635 R, 642

[56] References Cited

FOREIGN PATENT DOCUMENTS 2,175,689 10/1973 France

*Primary Examiner*—Winston A. Douglas
*Assistant Examiner*—P. E. Konopka
*Attorney, Agent, or Firm*—Olson, Trexler, Wolters, Bushnell & Fosse

[57] ABSTRACT

A process for the production of alcohols comprises hydroxylating a saturated hydrocarbon at between about 20° C. and about 130° C. with an oxygenated amine. The amine may be a hydroxylated secondary amine or an oxide of a tertiary amine. The reaction medium includes a Lewis acid and a salt of divalent or trivalent iron.

27 Claims, No Drawings

METHOD OF HYDROXYLATION

BACKGROUND OF THE INVENTION

This invention relates generally to methods for the preparation of hydroxylated organic compounds and more specifically to the introduction of a hydroxyl group into alkyl and alkylene constituents of organic compounds.

Although the introduction of hydroxyl groups into saturated aliphatic and alicyclic hydrocarbon compounds by microbiological means has been known for many years, satisfactory methods of direct hydroxylation of these structures by purely chemical procedures have not been available in the past. Many oxidative procedures are known which introduce oxygenated functions into saturated hydrocarbon chains; but in general, an undesirable mixture of alcohol, aldehyde, ketone and carboxylic acid results.

SUMMARY OF THE INVENTION

I have now found that organic compounds containing long alkyl or alkylene chains can be selectively oxidized with the replacement of a hydrogen atom by a hydroxyl group without the formation of higher oxidation products such as carbonyl and carboxyl derivatives. The omega-minus-one position appears to be the preferential situs for insertion of the hydroxyl group; and it is believed that a free radical mechanism is involved.

The present invention is useful in the production of hydroxylated fatty acids, which products have known utility in antibacterial agents and as starting materials for the preparation of polymers for coatings, plasticizers and lubricants. The present invention is especially advantageous in that the hydroxyl group is inserted in a position remote from the active, carboxyl substituent of the fatty acid molecule, rather than proximal thereto as might be expected if the reaction were to succeed at all.

It is therefore an important object of the present invention to provide a method of hydroxylating saturated hydrocarbon compounds which employs an intermolecular oxidation technique.

A more general object of the invention is to provide new and improved methods of hydroxylating saturated hydrocarbon compounds.

These and other objects and features of the invention will become apparent from a consideration of the following descriptions.

DESCRIPTION OF THE PREFERRED EMBODIMENT

According to the present invention, alcohols and esters are prepared from the corresponding saturated hydrocarbon by reacting the hydrocarbon compound with an N-oxygenated amine in a medium which includes a suitable Lewis acid, such as trifluoroacetic acid, and a salt of a first series transition metal element, such as ferrous carbonate. Upon completion of the reaction, the resultant product is separated from the processing medium, as by distillation, or by the addition of water followed by extraction with a water-insoluble organic solvent; and in the event that the reaction product is an ester and the corresponding alcohol is the desired end product, the ester is hydrolyzed to the free alcohol by conventional hydrolytic procedures.

Organic compounds useful as a starting material in the practice of the invention include alkanes and cycloalkanes having a chain length of at least four carbon atoms; and one or more of the hydrogen atoms in the compound may be substituted for by hydroxyl, carboxyl, carboxamide, lower carbalkoxy, halogen, alkoxyl and oxo moieties. In addition, the starting hydrocarbon compound has the general formula

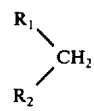

wherein $R_1$ and $R_2$ are alkyl groups which have a total of from 3 to 18 carbon atoms and wherein the dotted line represents an optional carbon-to-carbon bond. Specific hydrocarbon compounds which have proved particularly useful in the practice of the present invention include the following:

| | |
|---|---|
| heptane | 1-tetradecanol |
| decane | 2-octanone |
| cyclodecane | octanoic acid |
| cyclohexane | 1-octanoic amide |
| cycloctane | methyl octanoate |
| cyclododecane | methyl octyl ether |
| 1-pentanol | 1-chlorooctane |
| 1-octanol | 1-chloropentane |
| 1-decanol | 1-aminooctane |
| 1-dodecanol | 1-amino-octadecane |
| | stearic acid |

The oxidizing agent for use in inserting a hydroxyl group in the saturated hydrocarbons described immediately hereinabove is advantageously an N-oxygenated aliphatic or alicyclic amine or N-mono- and N,N,alkyl derivatives and takes the particular form of trialkyl amine oxides and N,N-dialkylhydroxylamines in which the alkyl groups contain a total of from 2 to 18 carbon atoms. Furthermore, the alkyl groups may be branched or they may be joined to form an oxygenated cycloalkylamine or they may be joined through an additional nitrogen atom to form mono- or bi-cyclic diamines. Useful alkylhydroxylamines include N,N-diethylhydroxylamine and N-hydroxypiperidine; and representative tertiary amine oxides include trimethylamine oxide, triethylamine oxide and 1,4-diaza-bicyclo(2.2.2)octane N,N-dioxide. In addition, a 0.5 to 2.5 molar excess of the oxidizing agent has been found to be associated with higher percentage yields of the ultimate ester or alcohol.

The medium for reaction of the saturated hydrocarbon compounds and the oxidizing agent comprises a Lewis acid and a catalyst taking the form of a salt of a first series transition metal element, salts of the described character being known initiators of free-radical reactions. Exemplary Lewis acids in this regard include strong organic acids, such as trifluoroacetic acid, mineral acids, such as sulfuric acid, and mixtures of organic and mineral acids. Trifluoroacetic acid has proved eminently suitable in the practice of the present invention but is costly; mixtures of 80% acetic acid and 20% sulfuric acid and 20 or 33% methanesulfonic acid in acetic acid is generally useful; and strong sulfuric acid has relatively poor solvent characteristics except in relation to molecules that are highly oxygenated.

As stated hereinabove, the catalyst for the reaction of the present invention comprises a salt of the first series transition metal elements, that is, salts of iron, cobalt, nickel, vanadium, copper and titanium; and while salts of these metals in their lower oxidation states are preferred, higher oxidation states may be employed inasmuch as these latter compounds revert to their lower oxidation states in the free radical situation. Examplary anions for these salts include carbonate, sulfate, acetate, hydroxide and ammonium sulfate.

Ferrous carbonate is a particularly advantageous catalyst, especially when the reaction medium is selected to include trifluoroacetic acid because the carbonate affords more of the active ferrous ion for a given addition in such an environment. Ferrous carbonate may be prepared by adding aqueous 10% sodium carbonate to boiling ferrous ammonium sulfate solution. A precipitate results and is subjected to multiple washings with distilled water, the water being separated after each washing by decantation. Desirably, the precipitated material is protected from atmospheric air and other sources of oxygen; and after the last washing, the wet ferrous carbonate is placed on a rotary evaporator at 100° C. and 20 torr. The resultant olive-green flakes are stored in a nitrogen atmosphere until use.

The reaction between the saturated hydrocarbon compound and the oxydizing agent proceeds with facility; and temperatures in the range of from about 20° C. to about 130° C. produce acceptable results in 5 days' time or less. Inert atmospheres of nitrogen or carbon dioxide are useful in increasing yields, although the reaction proceeds reasonably well even in an atmosphere of air. The reaction product itself may be extracted from the reaction medium with ethyl ether, carbon tetrachloride or other suitable solvents and then demoisturized over solid sodium sulfate and distilled.

When esters are the evident reaction product, they may be readily hydrolyzed to the corresponding alcohol if desired. Water at ambient room temperature slowly effects this hydrolysis, and it proceeds rapidly in the presence of strong bases at 25° C. and in boiling water.

In order to describe the invention more fully, the following specific examples are given without, however, intending to limit the invention to the precise details and conditions described except as is set forth in the appended claims.

EXAMPLE I

A reaction mixture was prepared by adding together 20.0 ml. of trifluoroacetic acid; 0.65 g. (5 mmol) of 1-octanol; 0.67 g. (6 mmol) of trimethylamine oxide de-hydrate; and 0.23 g. (2 mmol) of ferrous carbonate. This mixture was stirred under reflux and a carbon dioxide atmosphere at approximately 75° C. for 5 days. The resulting mixture was thereafter cooled and diluted to approximately 20% trifluoroacetic acid with ice water. The diluted mixture was extracted with ethyl ether and the ethereal liquid washed once with water and then with sufficient aqueous 10% sodium carbonate to give an alkaline solution. The ether extract was then washed a second time with aqueous 10% sodium carbonate and dried over solid sodium sulfate.

Gas chromatograms were obtained on a Barber-Colman Series 5000 instrument equipped with a flame ionization detector. The fuel gas was a mixture of hydrogen and air, and the carrier gas was nitrogen. The glass U-columns were 0.25 in. × 6 ft.; and 20% SE 30 on 80-100 Gas Chrom W was used at 150° C. Flow rates were 23 $ml.min^{-1}$.

The reaction products of the starting material were all present as the corresponding trifluoroacetates; and gas chromatographic analysis showed that 70% of the 1-octanol had been converted to octanediols in the following proportions:

| Hydroxy Substitution | Relative Proportion |
|---|---|
| 1,7 | 68% |
| 1,6 | 23 |
| 1,5 | 8.5 |
| 1,4 | 0.8 |

The identification of the foregoing reaction products was supported by nuclear magnetic resonance spectroscopy.

EXAMPLES II AND III

The general procedure of Example I was repeated substituting cyclohexane as the starting hydrocarbon material, using 100% stoichiometric excess of each of triethylamine oxide and diethylhydroxylamine in separate runs, and employing ferrous sulphate as the catalyst. Yields were on the order of 50% conversion of the starting material.

EXAMPLES IV AND V

The procedure of Example I was employed using decane as the starting hydrocarbon material, 40 mol-percent ferrous carbonate as catalyst, and a 10% excess of trimethylamine oxide. A conversion of 86% was obtained of which 81% was monohydroxylated and 5% was dihydroxylated.

Decane was also successfully hydroxylated in a medium comprising 20% sulfuric acid in acetic acid.

EXAMPLE VI

The procedure of Example I was again followed generally but utilizing cyclododecanol and trimethylamine oxide as the reactants, the latter in 100% excess. A 50% conversion was achieved.

EXAMPLES VII, VIII AND IX

Using the general procedure of Example I and employing 20% excess trimethylamine oxide as the oxidizing agent, 1-dodecanol and 1-tetradecanol were converted to the corresponding dihydroxy compounds and 2-octanone was converted to 7-hydroxy-2-octanone.

EXAMPLE X

Using the general procedure of Example I and 100% excess of trimethylamine oxide as the oxidizing agent, octanoic acid was converted to a mixture of the trifluoroacetates of hydroxyoctanoic acid in a 66% yield.

EXAMPLES XI, XII, XIII AND XIV

Octanoamide, 1-chlorooctane, stearic acid and methyl octyl ether were also successfully hydroxylated using trimethylamine oxide as the reactant.

The specific examples herein described are to be considered as being primarily illustrative only. Various changes beyond those described will, no doubt, occur to those skilled in the art; and such changes are to be understood as forming a part of this invention insofar as they fall within the spirit and scope of the appended claims.

The invention is claimed as follows:

1. The process of preparing alcohols by single-carbon hydroxylation, which comprises the steps of: reacting a saturated hydrocarbon compound with an N-oxygenated amine in a medium including a Lewis acid and a ferrous salt; and separating the reaction product from said medium.

2. The process according to claim 1 in which the N-oxygenated amine is a di-alkylsubstituted hydroxylamine compound.

3. The process according to claim 2 in which the di-alkylsubstituted hydroxylamine is a di-lower alkylhydroxylamine in which the alkyl groups contain a total of from 2 to 18 carbon atoms.

4. The process according to claim 3 in which the di-lower alkylhydroxylamine is N,N-diethylhydroxylamine.

5. The process according to claim 3 in which the di-lower alkylhydroxylamine is N-hydroxypiperidine.

6. The process according to claim 1 in which the N-oxygenated amine is selected from the group consisting of N-oxygenated aliphatic, alicyclic and heterocyclic amines.

7. The process according to claim 6 in which the amine oxide is trimethylamine oxide.

8. The process according to claim 6 in which the amine oxide is a cyclic aza-alkane oxide.

9. The process according to claim 8 in which the cyclic aza-alkane oxide is 1,4-diaza-bicyclo(2.2.2) octane N,N-dioxide.

10. The process according to claim 1 in which the Lewis acid is a strong organic acid.

11. The process according to claim 10 in which the strong organic acid is trifluoroacetic acid.

12. The process according to claim 1 in which the Lewis acid is sulfuric acid.

13. The process according to claim 1 in which the Lewis acid is a mixture of sulfuric acid and an organic acid.

14. The process according to claim 13 in which the organic acid is acetic acid.

15. The process according to claim 1 in which the Lewis acid is a mixture of methanesulfonic acid and acetic acid.

16. The process according to claim 1 in which the salt is ferrous carbonate.

17. The process according to claim 1 in which the salt is ferrous sulfate.

18. The process according to claim 1 in which the salt is ferrous acetate.

19. The process according to claim 1 in which the salt is ferrous hydroxide.

20. The process according to claim 1 in which the reaction is caused to take place at a temperature of from about 20° to about 130° C.

21. The process according to claim 1 in which the saturated hydrocarbon compound has the general formula $$\begin{matrix} R_1 \diagdown \\ \quad CH_2 \\ R_2 \diagup \end{matrix}$$

wherein $R_1$ and $R_2$ are alkyl groups which have combined a total of from 4 to 18 carbon atoms and wherein the dotted line represents an optional carbon-to-carbon bond.

22. The process according to claim 21 wherein $R_1$ and $R_2$ form an alicyclic ring.

23. The process according to claim 1 in which the saturated hydrocarbon is decane.

24. The process according to claim 1 in which the saturated hydrocarbon is heptane.

25. The process according to claim 1 in which the saturated hydrocarbon is cyclohexane.

26. The process according to claim 1 in which the saturated hydrocarbon is cyclooctane.

27. The process according to claim 1 in which the saturated hydrocarbon is cyclododecane.

* * * * *